United States Patent [19]

Picciolo et al.

[11] 4,132,599

[45] Jan. 2, 1979

[54] DETERMINATION OF ANTIMICROBIAL SUSCEPTIBILITIES ON INFECTED URINES WITHOUT ISOLATION

[76] Inventors: James C. Fletcher, Administrator of the National Aeronautics and Space Administration, with respect to an invention of Grace L. Picciolo, Tantallon, Md.; Emmett W. Chappelle, Baltimore, Md.; Jody W. Deming, Annapolis, Md.; Christian G. Shrock, Eding, Minn.; Hillar Vellend, Toronto, Canada; Michael J. Barza, Boston; Louis Weinstein, Newtonville, both of Mass.

[21] Appl. No.: 680,015

[22] Filed: Apr. 23, 1976

[51] Int. Cl.$^2$ ............................................... C12K 1/00
[52] U.S. Cl. ...................... 195/103.5 K; 195/103.5 L
[58] Field of Search .................. 195/103.5 R, 103.5 K

[56] References Cited

U.S. PATENT DOCUMENTS

| | | | |
|---|---|---|---|
| 3,616,253 | 10/1971 | D'Eustachio | 195/103.5 R |
| 3,745,090 | 7/1973 | Chappelle et al. | 195/103.5 R |
| 3,772,154 | 11/1973 | Isenberg et al. | 195/103.5 R |
| 3,933,592 | 1/1976 | Clendenning | 195/103.5 R |
| 3,940,250 | 2/1976 | Plakas et al. | 195/103.5 R |
| 4,014,745 | 3/1977 | Fletcher et al. | 195/103.5 R |

*Primary Examiner*—Alvin E. Tanenholtz
*Attorney, Agent, or Firm*—Ronald F. Sandler; John R. Manning; John O. Tresansky

[57] ABSTRACT

Method for the quick determination of the susceptibilities of various unidentified bacteria contained in an aqueous physiological fluid sample, particularly urine, to one or more antibiotics. A bacterial adenosine triphosphate (ATP) assay is carried out after the elimination of non-bacterial ATP to determine whether an infection exists. If an infection does exist, a portion of the sample is further processed, including subjecting parts of the portion to one or more antibiotics. Growth of the bacteria in the parts are determined, again by an ATP assay, to determine whether the unidentified bacteria in the sample are susceptible to the antibiotic or antibiotics under test.

21 Claims, No Drawings

DETERMINATION OF ANTIMICROBIAL SUSCEPTIBILITIES ON INFECTED URINES WITHOUT ISOLATION

ORIGIN OF THE INVENTION

The invention described herein was made in the performance of work under a NASA contract and by employees of the United States Government and is subject to the provisions of Section 305 of the National Aeronautics and Space Act of 1958, Public Law 85-568 (72 Stat. 435; 42 USC 2457), and may be manufactured and used by or for the Government for governmental purposes without the payment of any royalties thereon or therefor.

BACKGROUND OF THE INVENTION

The present invention relates generally to a method for determining the effectiveness of antimicrobial agents against bacteria. More particularly, the invention relates to a method for rapidly determining the effectiveness of antimicrobial agents against bacteria in physiological fluids.

A rapid and routine procedure for the determination of the effectiveness of known antimicrobial agents against various bacteria is very frequently of vital importance, particularly for the measurement of the effectiveness of antimicrobial agents against bacteria in physiological fluids such as urine. Present techniques for the determination of microbial susceptibility generally require at least overnight incubation of an infecting organism after it is first isolated and cultured. The prior art techniques, therefore, require a waiting period of two days because of the double culture requirement to test the effectiveness of antimicrobial agents after the fluid specimen is received for testing.

The most commonly used conventional techniques for the determination of microbial susceptibility to antimicrobial agents include agar diffusion (the Kirby-Bauer technique), broth dilution (Mic-Broth Dilution) and agar dilution. A long standing need continues to exist in practice for a rapid technique for determining microbial sensitivity to antimicrobial agents. A testing procedure is desirable therefore, which will allow the immediate treatment of a patient with a selective antibiotic or antibiotics which excludes the inclusion of inappropriate, unnecessary, and often toxic agents in the therapeutic regimen of an infected person.

The agar diffusion (Kirby-Bauer technique) method involves an overnight culture of a urine sample. The colonies of interest are separated out and an inoculum is obtained by dilution in trypticase soy broth (TSB), to such a concentration that a dense growth is observed. The culture turbidity is adjusted to a concentration which conforms to a turbidity standard. The standard is formed by mixing 0.5 ml of 0.048 M barium chloride (1.175% w/v Ba $Cl_2$—$2H_2O$) with 99.5 ml of 0.36 $(NH_4)_2SO_4$ (1% w/v). A sterile cotton swab is soaked in the diluted culture, and an agar plate is then streaked in four directions to obtain an even and thorough distribution of the organisms on the plate. The treated plates are dried for 15 minutes at 37° C. Thereafter, antibiotic discs are applied to the surface of the agar and pressed into place. The plates are then allowed to stand at room temperature for 30 minutes and incubated at 37° C. for 18 to 20 hours. A clearly defined zone will appear around an antibiotic disc where no bacterial growth has occurred. The zone diameter will vary with the relative resistance or susceptibility of the bacterial strain under test to the particular antibiotic used. The test must be replated for each original bacterial colony of interest. The chief disadvantage of this type of test is the time consumed to determine susceptibility.

The broth dilution (MIC-Broth Dilution) method of determing microbial sensitivity to antimicrobial agents involves visual detection of the least amount of antimicrobial agent required to cause complete inhibition of bacterial growth in a culture medium. In this technique, two-fold dilutions of antibiotics are made in a suitable culture medium. A control tube containing the culture medium, without an antibiotic, is also included for each organism tested. The organism is then allowed to grow to a logarithmic or early stationary phase of growth in the medium, and then diluted to a solution containing $10^4$ to $10^5$ viable units per milliliter. A quantity of the cultured medium is then placed in each tube of a series containing varying amounts of an antibiotic, and the tubes are allowed to incubate at 37° C. for 16 to 20 hours. Thereafter, the end point of the test is determined visually, as described above. A disadvantage of this technique, in addition to the relatively long time required to complete the test is that care must be taken to recognize that slight amounts of turbidity present may be caused by the inoculum itself and not by the growth of the organism.

The agar dilution method of determining microbial sensitivity to antimicrobial agents involves the same process as the broth dilution except that the process is modified to include the introduction of nutrient agar to the antibiotic dilutions, which become solid, so that a spot application of the diluted broth culture will result in the growth or no growth of the organisms on the agar surface.

SUMMARY OF THE INVENTION

Accordingly, one object of the present invention is to provide a rapid method for determining the sensitivity of bacterial organisms to antimicrobial agents.

Another object of the invention is to provide a method of measuring the sensitivity of microbial organisms present in a physiological fluid to various antimicrobial agents.

Yet another object of the invention is to provide a method of measuring the sensitivity of microbial organisms present in urine to multiple antimicrobial agents.

Still another object of the invention is to provide a method of measuring the sensitivity of microbial organisms present in a physiological fluid to various antimicrobial agents without isolation of each strain of organism present.

Another object of the invention is to provide a method of measuring antimicrobial sensitivity of bacteria in a routine system for chemical application.

Yet another object of the invention is to provide a method of measuring antimicrobial sensitivity of bacteria after determining a quantitated infection.

Briefly, these and other objects of the invention, as hereinafter will become more readily apparent, can be attained by a method for determining the sensitivity of bacteria to antimicrobial agents by measurement of an ATP index by the following procedure. First, there must be a determination as to whether or not an infection exists.

This determination is made by means of a bacterial ATP luminescent assay of a physiological fluid sample, for example, urine, which is correlated with a bacterial count. If the bacterial count is below approximately 3 × 10⁴CFU/ml for urine, the patient is not normally considered to have an infection. With respect to blood almost any count at all would be considered to be an infection. All specimens should be collected in an essentially sterile fashion.

Assuming there is an infection, another portion of the same fluid must be tested with respect to one or more antibiotics to determine if the dominant bacterial strain or strains are susceptible to the antibiotic or antibiotics under test. Broth is added to this second portion to achieve a working inoculum and the resulting inoculum is preincubated. At this point a minimum of three samples are aliquoted for one antibiotic under test. While the remaining discussion will relate to the susceptibility testing of a particular fluid vis-a-vis one antibiotic, it should be understood that the same methodology would be repeated in order to test a multiplicity of antibiotics. The sample to be tested with an antibiotic should now have the antibiotic added; the remaining two samples will have an equivalent volume of water added. One sample without antibiotic is immediately assayed for bacterial ATP while the remaining one sample without antibiotic and the remaining one sample with antibiotic are incubated at about 37° C. for about 2.5 hours and then they are assayed for bacterial ATP content. All bacterial ATP assays are carried out by obtaining light readings by reacting bacterial ATP with a luciferase-luciferin mixture. The assay results, in terms of light units, are placed in an empirical equation defining an "ATP index" of inhibition i.e., an index indicating whether the bacteria causing the infection are generally resistant to the antibiotic under test. The equation is:

$$\text{ATP index} = (B_{2.5} - A_0)/(A_{2.5} - A_0),$$

where
$B_{2.5}$ is the reading for the sample with the antibiotic after incubation for 2.5 hours.
$A_{2.5}$ is the reading for the sample without antibiotic after incubation for 2.5 hours; and
$A_0$ is the reading for the sample without antibiotic without incubation.

It has been determined that an ATP index of greater than 0.05 is an indication that the dominant bacterial strain or strains present are generally resistant to the antibiotic tested.

DETAILED DESCRIPTION OF THE PREFERRED EMBODIMENTS

Basic bacterial ATP assay methodology is now well known in that art. The first requirement for making a bacterial ATP assay of a sample is to free all non-bacterial sources of ATP and selectively destroy this ATP, otherwise the bacterial ATP readings will be inaccurate. Next, the bacterial cells are ruptured to free their ATP without destruction. A bacterial ATP assay can then be carried out by reacting the bacterial ATP with a luciferase-luciferin compound to obtain a light reaction proportional to the ATP present. The light reaction can be converted to a measurement of ATP present which, in turn, can be related to a bacterial count. In conducting bacterial ATP assays for the purposes of carrying out the instant invention, there is no need to obtain a bacteria count; only light readings need be obtained. One bacterial ATP assay process is disclosed in U.S. Pat. No. 3,745,090 issued to Chappelle et al. An improved, more sensitive process, is disclosed in U.S. Pat. Application Ser. No. 555,641, Picciolo et al, now U.S. Pat. No. 3,971,703. Their disclosures are incorporated by reference and both of common assignee herewith. It should be understood that these prior inventions deal only with bacterial ATP assays using a light reaction, converting the light reading to an ATP reading and, thereafter, correlating the ATP reading with a bacteria count. They contain no disclosure relating to the determination of bacterial susceptibility to a given antimicrobial agent. It has previously been known to use bacterial ATP assay techniques and the ATP index approach to determine bacterial susceptibility to antimicrobial agents but the previous method required the isolation and culturing of each dominant bacterial strain found in the physiological fluid sample. The present method is less time consuming, time being of the essence in many cases. The present invention provides a rapid determination of bacterial susceptibility to one or more antimicrobial agents by recognizing that isolation of various bacteria in a physiological fluid is not required to form a meaningful ATP index i.e., all that is required is the determination of whether or not a particular antibiotic is generally effective against the dominant bacterial strains present in the sample under test.

The process of this invention is generally useful with respect to any physiological fluid where enough fluid to perform the required steps can be obtained and the fluid contains a sufficient bacterial concentration to represent infection. The physiological fluids to which the invention is particularly applicable are urine, spinal fluid, pleural fluid, sputum, blood, acites and milk. The detailed discussion relates to the use of urine, one of the easier fluids to work with. When working with blood, the red and white blood cells need to be first removed, for example, by slow centrifugation, since they would act as inhibitors in the process. With respect to any fluid, the process inhibitors must be removed. With respect to a thick fluid, such as mucus, a non-interfering solvent would have to be used.

In the adaption of this technique for the determination of bacterial susceptibility to one or more antibiotics, it was initially required to determine if an infection is present. If there is no infection the process is, of course, aborted. With each type fluid sample and each type of collection system used to get the sample, a somewhat arbitrary level of bacteria count per milliliter should be established as a threshold which must be exceeded for an infection to be considered to exist. With urine specimens obtained by common collection methods the generally accepted figure is $3 \times 10^4$CFU/ml. therefore, as a first step, when the process involves a urine sample, a determination has to be made as to whether or not an infection exists, i.e., whether the sample contains 30,000 bacteria per milliliter.

When a urine specimen is received, about a 35 ml sample size is retained and concentrated, by centrifugation or filtration, to remove the liquid or supernatant phase. The preferred method for accomplishing this result is to centrifuge at 8000 rpm for 15 minutes to obtain a pellet. The sample and resulting pellet should be kept at a low temperature, about 4° C., to avoid bacterial growth. The purpose of this step is to eliminate the supernatant phase, which would interfere with bacterial growth, and obtain a pellet of concentrated bacteria (and other solid, particulate matter such as white and red blood cells). The speed of the centrifuge should be sufficient to separate out bacteria from the supernatant phase but not of such magnitude as to rupture bacterial cells or remove any bacterial ATP. The volume of urine required for the test depends on the number of antibiotics to be tested and the concentration of bacteria present. A 10 ml urine sample appears to be the minimum.

The pellet is now reconstituted by adding a liquid growth medium, preferably about 1.75 ml of trypticase soy broth (TSB). This is sufficient to provide two working portions; one for immediate determination of bacterial concentration to define whether an infection is present and the other for later antibiotic susceptibility testing. There is, therefore, a 20-times concentration of whatever bacterial concentration was present in the original specimen. Probably no less than 1.5 ml should be used. The resultant fluid is then vortexed, by hand or preferably machine to distribute the pellet in the broth. Two portions are then measured out, one for the detection assay and one for the antibiotic susceptibility test. In general 0.5 ml is used for the detection assay and about 1.25 ml is used for the antibiotic susceptibility test. The portion used for the antibiotic susceptibility test (if an infection is determined to exist) is stored at about 4° C. to prevent growth of the bacteria present. As with the previously noted centrifuging step temperature, 4° C. appears to be an excellent temperature choice to prevent bacteria growth. For one thing, the portions can not be allowed to go below their freezing point because the bacteria will rupture. For another, the portions can not be allowed to go above a temperature whereby the bacteria will significantly multiply or change their ATP levels during the period they are standing by for use. At this point, the 0.5 ml and 1.25 ml portions are processed and standing by for use; the 0.5 portion is ready for the detection assay and the 1.25 ml portion is stored for the later possible antibiotic susceptibility testing.

To the 0.5 ml portion a detergent and a hydrolyzing enzyme for the ATP (an ATP-ase) is added. The detergent must be capable of selectively rupturing (lysing) non-bacterial cells so that their ATP is made soluble. The hydrolyzing enzyme must be capable of hydrolyzing the ATP when it is made soluble by the detergent. One particularly suitable combination is TRITON X-100 (TX) for the detergent and apyrase for the enzyme, being present prior to and after lysing of the non-bacterial cells. More specifically, 0.1 ml of 10 mg/ml apyrase in 0.03M $CaCl_2$ and 0.1% TX is added to the 0.5 ml portion, volume by volume, the $CaCl_2$ furnishing calcium as a necessary cofactor for the apyrase.

The resulting solution is vortexed and a 0.9% NaCl weight by volume solution of sterile deinoized water added to bring up the volume to wash the sides of the tube being used. The criteria for the solution used is that it can not be hypotonic or hypertonic to the bacterial cells present. The solution is again vortexed and enough time allowed to lapse for the apyrase to take effect, the TX working immediately. A typical time period is 15 minutes, however, the time necessary is ultimately dependent on ATP present.

The next step in the process is to free membrane bound ATP into solution so that it also is available for destruction by the already present apyrase. The amount of bound ATP present can be small or large since it is related, to a great extent, to the number of blood cells present. If the bound ATP were left present in the fluid, it would be counted along with bacterial ATP indicating a greater bacterial count than actually present. Malic acid is added to free the bound ATP, specifically 1 ml of 0.25 M malic acid, which is prepared from sodium malate and adjusted to a pH of 4.25. The solutuion is vortexed. If an excessive amount of malic acid is added it interferes with the action of the nitric acid to be added later. If too little is added, the pH will be insufficient to allow desorbtion of ATP. The apyrase hydrolyzes the previously bound ATP during the next step.

At this stage of the process, the solution is concentrated to remove the liquid phase and, concomitantly, the interfering compounds. It is especially important to remove the apyrase so that the later acquired bacterial ATP is not hydrolyzed. The concentration step is again centrifuging at 8000 rpm for 15 minutes at 4° C. Filtration or other concentration techniques may be employed.

An extracting agent is added to rupture the bacterial cells thereby to free the bacterial ATP to permit measurement of the bacterial ATP and relate it to a bacteria count. Any extractant may be used which will release the bacterial ATP without any substantial hydrolyzing or other destruction of the ATP, i.e., 0.2 ml 0.1N $HNO_3$ left to operate about 5 minutes. The solution is now diluted and vortexed to weaken the acid concentration so that it will not interfere with the later described luciferase-luciferin reaction, i.e., the hydrogen ion concentration must be reduced or else the acid will diminish the light reaction between the ATP present and the luciferase-luciferin. For this purpose 0.2 ml sterile, deionized water may be used, sometimes with sodium sulfate in solution which is good for blank light level depression when the light level is measured.

After addition of the above-disclosed water and vortexing, the ATP, which is bacterial ATP, is assayed to obtain a working estimate of the bacteria count. The assay procedure is the same as described in the above-identified references which basically involved taking the resulting solution with bacterial ATP and reacting it with a luciferase-luciferin mixture and, thereafter, placing the solution into a light-tight chamber of a photometer. The resulting light reading is equated to an ATP reading which in turn, is correlated with a bacteria count. The amount of solution required at this point in the process is a minimum of 0.4 ml which is, in effect, a 25 times concentration of the original urine sample. If the reading indicates a bacterial count below $3 \times 10^4$CFU/ml an infection is not normally considered to be present and the process would be terminated here, i.e., there would be no testing for antibiotic susceptibility. Assuming the reading to be over a $3 \times 10^4$CFU/ml bacteria count, the next series of steps is then undertaken to determine the bacterial susceptibility to one or more antibiotics.

At this stage, broth is added to the previously stored second portion to achieve a working inoculum. The second portion is preferably a minimum of 1.25 ml. The object is to achieve a working inoculum size for the antibiotic susceptibility test that will provide results which correlate well with the traditional Kirby-Bauer test. Ideally a $10^5$ to $10^6$CFU/ml range is desired in the 1.25 ml portion. If a marginal infection exists, a minimum of broth is added so that the portion still has a growth medium but only to the point where the portion has a 1.5 ml volume. If a heavy infection is present, significant dilution is required to enable the resulting solution to have a $10^5$ to $10^6$CFU/ml bacterial concentration.

The solution is now pre-incubated to get the organisms present into log phase growth. The generally used procedure is to preincubate at 37° C., which simulates body temperature. In any event, the time period used must be of sufficient duration for log phase growth to begin for most bacteria present at whatever temperature is employed. A 20° C. to 45° C. temperature range has been found suitable.

After pre-incubation is completed, at least three aliquots of preferably, at least 0.45 ml each are divided out. The 0.45 ml figure is related to the normally used working volume of urine employed. These three aliguots form the three minimum samples required for antibiotic susceptibility testing of one antibiotic. An antibiotic is added to one sample. To the other two samples sterile, dionized water is added to compensate for the volume of antibiotic added to the first sample. By matching the volume of the antibiotic present, bacterial concentration equivalency is maintained at that point to maintain testing integrity. In general about 0.05 ml of antibiotic or water is added to each sample. If a multiple of antibiotics are used, the concentrations are varied to achieve the same volume for a working dosage that is added to a sample. If this is done, only one additional 0.45 ml sample is required for each antibiotic under test. The amount of antibiotic used is essentially dependent on the amount of the urine available.

At this stage one sample with antibiotic and one sample without antibiotic are placed into an incubator, the third sample, without antibiotic is immediately assayed according to the assay procedure herein before disclosed for infection determination, except that a less specific method, i.e., a method eliminating the malic acid addition to ultimately destroy bound ATP, may be employed. The reason for this is that in this test only relative, not absolute levels of bacterial ATP need be measured. The other two samples are incubated usually for 2.5 hours, to get the organisms into a log growth pattern. The incubation again is at 37° C. but can be within the range of about 20° C. to 45° C. Some bacteria are slow growing and would require additional time to achieve log growth. Of course, lower temperature incubation would also require a longer incubation period. Typically, the range is 0.5 to 10 hours. The 2.5 hour period at 37° C. is, however, generally sufficient. Upon completion of the incubation period, the incubated samples are assayed. (Again, there will be more than two samples if more than one antibiotic is under test.) The assay results on all three samples, in terms of light units, are placed into the equation:

ATP index = $(B_t - A_O)/(A_t - A_O)$ where
$B_t$ represents a light reading for a sample treated with antibiotic and allowed to incubate for a time "t";
$A_t$ represents a light reading for a sample not treated with antibiotic and allowed to incubate for a time "t"; and
$A_O$ represents a light reading for a sample not treated with antibiotic and not allowed to incubate taken at time zero.

The ATP index can also be determined according to the equation:

ATP index = $(\log B_t - \log A_O)/(\log A_t - \log A_O)$

If the ATP index is equal to or greater than 0.05 in the former equation or greater or equal to 0.25 in the latter equation the dominant bacterial strains generally present are considered to be resistant the antibiotic for which the index is obtained. In terms of clinical practice, the result would be interpreted as meaning that the antibiotic tested should not be used to cure the infection present.

The invention is further illustrated by the following working example which is illustrative of results obtained with one embodiment of the invention and is provided to teach those skilled in the art how to practice the invention with respect to one mode contemplated for carrying out the invention.

EXAMPLE (a) A 35 ml urine sample was centrifuged at 8000 rpm for 15 minutes at 4° C. to form a pellet and eliminates the liquid phase.

(b) The pellet was reconstituted by adding 1.75 ml of TSB obtain a 20 times concentration to the original sample.

(c) The solution was vortexed to distribute the pellet in the broth.

(d) Two portions of the solution were measured out, the first portion being 0.5 ml and the second portion being 1.25 ml.

(e) The second portion was stored at 4° C.

The following relates to processing of the first portion.

0.1 ml of a 10 mg/ml concentration of apyrase in 0.03M $CaCl_2$ and 0.1% TX, was added per 0.5 ml of the first portion.

(g) The portion was vortexed.

(h) 5 ml of 0.9% weight by volume saline solution of sterile, deionized water was added to the first portion.

(i) The portion was vortexed and allowed to stand for 15 minutes.

(j) 1 ml of 0.25 M malic acid at a pH of 4.5 was added to the portion.

(k) The portion was centrifuged at 8000 rpm for 15 minutes at 4° C. to form a pellet.

(l) 0.2 ml 0.1 N $HNO_3$ was added to the portion which was allowed to stand for 5 minutes to lyse the bacterial cells.

(m) The portion was diluted with 0.2 ml of a sterile, deionized water or with a 0.15 M sodium sulfate solution.

(n) The sample was then assayed for ATP by reacting it with a luciferase-luciferin solution to determine if the bacterial count is at least $3 \times 10^4$ CFU/ml.

Assuming the infection exceeds $3 \times 10^4$ CFU/ml the process is continued with the second portion (o) To the second portion enough TSB was added in order to achieve a working inoculum of form between $10^5$ and $10^6$ CFU/ml.

(p) The portion was pre-incubated for ½ hours at 37° C. in order to get the bacteria into log phase growth.

(q) Three 0.45 ml aliquots were divided out to form three samples.

(Alternatively the aliquots may be developed prior to incubation.)

(r) To one sample was added 0.05 ml of antibiotic (s) To other two samples was added 0.05 ml each of sterile, deionized water.

(t) One of the two samples without antibiotic was immediately assayed for ATP in terms of light units without bothering to destroy bound ATP.

(u) The remaining two samples were incubated for 2.5 hours at 37° C. and, thereafter, assayed in a fashion similar to the assay in step "t".

Note: The assays required in "(t)" and "(u)" can be any ATP assay which may or may not first destroy the bound ATP. One possible assay procedure is:

(1) add 0.1 ml of 10 mg apyrase/ml, 0.03 M $CaCl_2$ plus 0.6% TX-100 to the sample to be assayed;
(2) vortex and allow to stand for 15 minutes;
(3) add 0.1 ml 1.5 N $HNO_3$;
(4) vortex and allow to stand for 15 minutes;
(5) add 4.3 ml $H_2O$ or 0.085 M $Na_2SO_4$;
(6) vortex; and
(7) assay by injecting into a luciferaseluciferin mixture.

(v) The assay results were placed into the equation:

$$\text{ATP index} = (B_{2.5} - A_0)/(A_{2.5} - A_0)$$

where $B_{2.5}$ represents a light reading for the sample treated with antibiotic and allowed to incubate for 2.5 hours;

$A_{2.5}$ represents a light reading for the sample not treated with antibiotic and allowed to incubate for 2.5 hours; and $A_0$ represents a light reading for a sample not treated with antibiotic and not allowed to incubate, taken at time zero.

(w) An ATP index of 0.05 or greater would indicate that the dominant bacterial strains present are generally resistant to the antibiotic under test and that the antibiotic should not be used in treatment of the infection; an ATP index of less than 0.05 would indicate that the dominant bacterial strains present are generally susceptible to the antibiotic under test and that the antibiotic could be used in treatment of the infection.

The method of the instant invention, as disclosed herein, results in an improved method of determining bacterial susceptibility to antimicrobial agents, especially in a clinical environment. The method is, of course, also adaptable to a laboratory environment.

The method is not only suitable for use with urine samples, but is also adaptable to the determination of bacterial susceptibility to antimicrobial agents where the bacteria is carried in other physiological fluids.

The principles, preferred embodiments and modes of operation of the present invention have been described in the foregoing specification. However, the invention which is intended to be protected herein, is not to be construed as limited to the particulars disclosed since these are to be regarded as illustrative rather than restrictive. Variations and changes may be made by those skilled in the art without departing from the spirit of the present invention.

We claim:

1. A method for determining the general susceptibility of bacteria constituting a quantitated infection in a physiological fluid sample to antimicrobial agents without isolation of any individual bacterial strains that may be present by measurement of an ATP index indicating susceptibility, which comprises:

forming a solid containing bacteria by eliminating the liquid phase from the physiological fluid sample;

reconstituting the sample to a liquid by adding an aqueous growth medium to achieve a working inoculum;

pre-incubating the treated sample containing all the bacterial strains present in the physiological fluid to achieve log growth and dividing the sample into at least three portions;

adding sterile water to two portions and an antibiotic to each remaining portion and assaying one portion of said two portions without antibiotic for ATP;

incubating all other portions for a time sufficient for the antibiotic or antibiotics to take effect against the bacteria present, assuming the antibiotic to be effective;

assaying said all other portions for ATP; and determining the ATP index to indicate sensitivity of the bacteria to the antibiotic according to the formula $$\text{ATP index} = (B_t - A_0)/(A_t - A_0),$$

where $B_t$ represents an ATP assay reading for the portion or portions treated with an antibiotic and allowed to incubate;

$A_t$ represents an ATP assay reading for the portion not treated with antibiotic and allowed to incubate; and $A_0$ represents an ATP assay reading for the portion not treated with antibiotic and not allowed to incubate.

2. A method for determining the general susceptibility of bacteria constituting a possible infection in a urine sample to antimicrobial agents without isolation of any individual bacterial strains that may be present by measurement of an ATP index indicating susceptibility, which comprises:

forming a solid containing bacterial and non-bacterial cells by eliminating the liquid phase from the urine sample;

reconstituting the sample to a liquid by adding a growth medium;

measuring out first and second portions;

storing the second portion under conditions preventing significant bacterial growth;

thereafter treating the first portion by:

adding a hydrolyzing enzyme capable of hydrolyzing ATP and a detergent capable of rupturing non-bacterial cells;

adding an agent capable of freeing bound ATP from non-bacterial cells;

forming a solid containing bacterial cells;

rupturing the bacterial cells;

assaying the treated first portion for ATP to determine the presence of an infection;

adding an aqueous growth medium to the second portion to achieve a working inoculum;

pre-incubating the treated second portion containing all the bacterial strains present in the urine sample to achieve log growth and dividing the second portion into at least three samples;

adding sterile water to two samples and an antibiotic to each remaining sample and assaying one sample of said two samples without antibiotic for ATP;

incubating the all other samples for a time sufficient for the antibiotic or antibiotics to take effect against the bacteria present, assuming the antibiotic to be effective;

assaying said all other samples for ATP; and determining the ATP index to indicate sensitivity of the bacteria to the antibiotic according to the formula:

$$\text{ATP index} = (B_t - A_0),$$

where
- $B_t$ represents an ATP assay reading for the sample or samples treated with an antibiotic and allowed to incubate;
- $A_f$ represents an ATP assay reading for the sample not treated with antibiotic and allowed to incubate; and
- $A_0$ represents an ATP assay reading for the sample not treated with antibiotic and not allowed to incubate.

3. A method for determining the general susceptibility of bacteria constituting a possible infection in a physiological fluid to antimicrobial agents without isolation of particular bacteria by measurement of an ATP index indicating susceptibility, which comprises:

assaying a portion of the fluid for ATP to determine the existence of an infection; and dividing a remaining portion of the fluid into at least three samples before or after pre-incubation to have bateria which are all those strains present in the untreated physiological fluid present enter log phase growth;

adding sterile water to two samples and an antibiotic to each remaining sample and assaying one sample of said two samples without antibiotic for ATP;

incubating all other samples for period sufficient for significant bacterial growth in the absence of an effective antibiotic;

assaying said all other samples for ATP; and determining the ATP index to indicate sensitivity of the bacteria to the antibiotic according to the formula:

$$\text{ATP index} = (B_t - A_0),$$

wherein
- $B_f$ represents an ATP assay reading for the sample or samples treated with an antibiotic and allowed to incubate;
- $A_f$ represents an ATP assay reading for the sample not treated with antibiotic and allowed to incubate; and
- $A_0$ represents an ATP assay reading for the sample not treated with antibiotic and not allowed to incubate.

4. The method of claim 1 wherein said bacteria are derived from a body fluid selected from the group consisting of urine, ascites, lymph fluid, plasma, blood, spinal fluid, saliva and mucus.

5. The method of claim 1 wherein said solid is formed by centrifugation.

6. The method of claim 1 wherein said growth medium is trypticase soy broth.

7. The method of claim 1 wherein the working inoculum is from between $10^5$ and $10^6$ CFU/ml.

8. The method of claim 1 wherein pre-incubation is for about ½ hour at about 37° C.

9. The method of claim 1 wherein incubation is for about 2.5 hours at about 37° C.

10. The method of claim 1 wherein all ATP assays are light readings.

11. The method of claim 2 wherein the solid is a pellet formed from the urine sample by centrifuging at about 8000 rpm for about 15 minutes at 4° C.

12. The method of claim 2 wherein the solid is reconstituted by adding sufficient trypticase soy broth to obtain about a twenty-times concentration of the urine sample.

13. The method of claim 2 wherein said first and second portions are at least about 0.5 ml and 1.25 ml, respectively.

14. The method of claim 2 wherein the second portion is stored at about 4° C.

15. The method of claim 2 wherein the hydrolyzing enzyme and detergent are apyrase and octylphenoxyl plyethoxyethanol, respectively.

16. The method of claim 2 wherein the agent capable of freeing bound ATP is malic acid.

17. The method of claim 2 wherein the solid containing bacterial cells is a pellet formed by centrifuging at about 8000 rpm for about 15 minutes at about 4° C.

18. The method of claim 2 wherein the bacterial cells are ruptured by the addition of nitric acid.

19. The method of claim 2 wherein trypticase soy broth is added to the second portion to achieve a working inoculum of from about $10^5$ to $10^6$ CFU/ml.

20. The method of claim 2 wherein pre-incubation of the treated second portion is for about 0.5 hours and at about 37° C.

21. The method of claim 2 wherein incubation of the samples is for about 2.5 hours and at about 37° C.

* * * * *